US007151070B2

(12) United States Patent
Gong et al.

(10) Patent No.: US 7,151,070 B2
(45) Date of Patent: Dec. 19, 2006

(54) CHIRAL CATALYST, PROCESS FOR PREPARING THE SAME AND ITS USE IN THE OXIDATE COUPLING OF NAPHTHOLS

(75) Inventors: Liuzhu Gong, Sichuan (CN); Zhibin Luo, Sichuan (CN); Quanzhong Liu, Sichuan (CN); Aiqiao Mi, Sichuan (CN); Yaozhong Jiang, Sichuan (CN)

(73) Assignee: Chengdu Institute of Organic Chemistry Chinese Academy of Sciences, Sichuan (CN)

( * ) Notice: Subject to any disclaimer, the term of this patent is extended or adjusted under 35 U.S.C. 154(b) by 0 days.

(21) Appl. No.: 10/518,118

(22) PCT Filed: Feb. 27, 2003

(86) PCT No.: PCT/CN03/00156

§ 371 (c)(1), (2), (4) Date: Dec. 15, 2004

(87) PCT Pub. No.: WO03/106467

PCT Pub. Date: Dec. 24, 2003

(65) Prior Publication Data

US 2005/0256345 A1    Nov. 17, 2005

(30) Foreign Application Priority Data

Jun. 18, 2002    (CN) ................................ 02 1 33305

(51) Int. Cl.
    *B01J 31/00*    (2006.01)
(52) U.S. Cl. ................ 502/102; 502/103; 502/104; 502/150; 568/735; 556/32; 556/42
(58) Field of Classification Search ................ 502/102, 502/150, 103, 104; 568/735; 556/32, 42
    See application file for complete search history.

(56) References Cited

U.S. PATENT DOCUMENTS

| 5,952,532 | A  | * | 9/1999  | Durante et al. ............. 568/802 |
| 5,981,424 | A  |   | 11/1999 | Durante et al. |
| 6,166,261 | A  | * | 12/2000 | Takahashi .................... 568/344 |
| 6,180,788 | B1 | * | 1/2001  | Stibrany ...................... 544/225 |
| 6,214,761 | B1 | * | 4/2001  | Bennett ....................... 502/117 |
| 6,232,510 | B1 | * | 5/2001  | Barnhart ..................... 568/802 |
| 6,265,622 | B1 | * | 7/2001  | Barnhart ..................... 568/802 |
| 6,410,805 | B1 | * | 6/2002  | Barnhart ..................... 568/802 |
| 6,417,305 | B1 | * | 7/2002  | Bennett ....................... 526/161 |
| 6,432,862 | B1 | * | 8/2002  | Bennett ....................... 502/117 |
| 6,646,167 | B1 | * | 11/2003 | Tsuruya ....................... 568/802 |
| 6,677,496 | B1 | * | 1/2004  | Netzer ......................... 585/648 |
| 6,747,105 | B1 | * | 6/2004  | Chen et al. .................. 526/160 |
| 6,875,718 | B1 | * | 4/2005  | Fujita et al. ................. 502/103 |

FOREIGN PATENT DOCUMENTS

WO    WO 94/03271 A1 *    2/1994

OTHER PUBLICATIONS

Liu, et al. "Schiff base complexes of vanadium (III, IV, V) as catalysts for the electroreduction of O2 to H2O in Acetonitrile", Inorg. Chem. 2001, 40, 1329-1333.*
www.sci.u-szeged.hu/kkk/vanadium4/Pessoa1.pdf.*

* cited by examiner

*Primary Examiner*—J. A. Lorengo
*Assistant Examiner*—Jennine Brown
(74) *Attorney, Agent, or Firm*—Greer, Burns & Crain, Ltd

(57) ABSTRACT

The compound of this invention is a useful catalyst for the oxidative coupling of naphthol. Its originality lies in that it is a novel vanadium complex of Schiff's base formed by a chiral amino acid and a formyl biphenol or its derivative. Its axis chirality is induced to form by the chiral amino acid. It has the general formula:

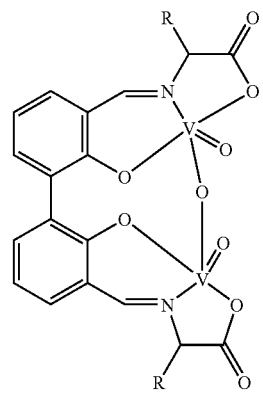

where R represents a benzyl, an isopropyl, an isobutyl or a tertiary butyl and the configuration of the amino acid is R or S. The compound can catalyze oxidative coupling of naphthol or its derivative to form binaphthol or its derivatives with a high optical purity.

14 Claims, No Drawings

CHIRAL CATALYST, PROCESS FOR PREPARING THE SAME AND ITS USE IN THE OXIDATE COUPLING OF NAPHTHOLS

FIELD OF THE INVENTION

The present invention relates generally to asymmetric catalysis in the field of organic chemistry. More particularly, the invention relates to a type of chiral catalyst and its use in asymmetric oxidative coupling of 2-naphthols.

The invention also relates to the preparation of the above-mentioned catalysts.

The invention also relates to the use of the above-mentioned catalysts in preparation of binaphthol and its derivatives.

DESCRIPTION OF THE RELATED ART

The optically pure binaphthol with axial chirality has been one of the warmest research area for organic chemists not only because it has been used as building blocks for the construction of many important natural products, (*Tetrahedron* 1995, 51, 9353; *Tetrahedron* 2000, 56, 2325), but also because binaphthol and its derivatives have been extensively used as chiral auxiliaries and ligands in asymmetric synthesis, and shown extremely high stereo-control property in a wide range of asymmetric transformations. (*Chem. Rev.* 1992, 92, 1007; Chem. *Rev.* 1992, 92, 1021; *Chem. Rev.* 1998, 98, 2405; *Asymmetric Catalysis in Organic Synthesis; Wiley and Sons: The New York,* 1994). The importance of such molecules has fuelled the development of efficient methodologies to prepare them. There are mainly three existed methods for the preparation of optically pure binaphthols:

1. Resolution of Racemate Binaphthol.

Resolution is the most efficient and important method for the preparation of optically pure binaphthol at the present time. This method includes the firstly oxidative coupling of 2-naphthol to binaphthol catalyzed by a chiral catalyst and subsequently inclusion resolution or chemical resolution to obtain the optically pure form of binaphthol. But when the resolution method was used, an equal amount of resolution reagent was needed, and usually these resolution reagents were expensive, further more, no more than 50% yield of the optically pure product can be obtained from resolution of racemate. These drawbacks limited the practical application of the resolution method. [*Bioorg. Chem.* 1978, 7, 7397; *J. Org. Chem.* 1998, 53, 3607; *Tetrahedron Lett.* 1987, 28, 355; *J. Org. Chem.* 1981, 46, 4988; *Tetrahedron Asymmetry* 1995, 6, 2123; *Tetrahedron Lett.* 1995, 35, 7991].

2. Nonoxidative Coupling Synthetic Method.

Optically pure binaphthol and its derivatives can also be obtained from coupling reaction catalyzed by metal complexes. Tamio Hayashi group reported the coupling of Grignard reagent with bromobenzene catalyzed by Ni complexes, giving binaphthol derivatives in up to 95% e.e. [*J. Am. Chem. Soc.* 1988, 110, 8153]. But the ligand used in this reaction was rather expensive, and the substrate scope was limited. Tomioka also synthesized similar compounds through nucleophilic substitution in 1992. [*J. Am. Chem. Soc.* 1992, 114, 8732] Other methods such as Suzuki reaction and Heck reaction were also used for the preparation of binaphthol derivatives with axial chirality. [*Chem. Commun,* 2000, 1723; *J. Am. Chem. Soc.* 2000, 122, 12051]. All these methods were restricted by the same drawbacks: limited substrate scope, the ligands were expensive and difficult to prepare in large scale, and when scaled up, the catalytic reaction was difficult to maintain high enantioselectivity.

3. Oxidative Coupling Reaction

Oxidative coupling reaction provided the method of directly converting optically nonactive 2-naphthols into optically pure binaphthol and its derivatives using $O_2$ as oxidant in the presence of catalytic amount of chiral catalyst. This method received extensive recognition because only catalytic amount of catalyst was needed, other oxidant and substrates were easy to obtain, and the coupling products were optically pure binaphthol and its derivatives with very important function in organic synthesis. For this method the difficulty lies in the design and synthesis of chiral ligand. By far there are two relatively successful research works in this area were reported: Oxidative coupling of 2-naphthol derivatives catalyzed by chiral Ru(II)-Imine complexes gave corresponding binaphthols in 33–71% e.e. [*Synlett,* 2000, 333], usually the products from this method have low optical purity and can not be used directly; When chiral V(IV)-Shiff base complexes were used as catalysts, up to 62% e.e of the product was obtained for oxidative coupling of 2-naphthol. [*Chem. Commun.* 2001, 3, 869; *Org. Lett.* 2001, 66, 481].

SUMMARY OF THE INVENTION

One objective of this invention is to provide a type of chiral catalyst used for oxidative coupling of 2-naphthol, giving binaphthol with high optical purity.

Another objective of this invention is to provide a preparation method for the chiral catalyst used in oxidative coupling of 2-naphthols.

The other objective of this invention is to provide the use of this type of chiral catalyst in the preparation of optically pure binaphthol and its derivatives.

The objectives of this invention were realized through following technical project:

The characteristic of the chiral catalyst used in oxidative coupling of 2-naphthol is a complex of vanadium and Shiff base derived from the condensation of chiral amino acid with 3,3'-diformyl-2,2'-dihydroxy-1,1'-phenyl, structure of the catalyst was shown below:

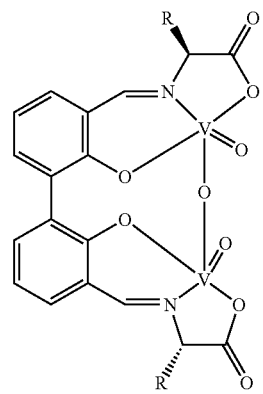

Wherein R is either benzyl, phenyl, isopropyl, isobutyl or tertbutyl; The configuration of the amino acid is R or S.

In accordance with the present invention, the procedure for preparation of chiral catalysts was described as follows: Chiral amino acid and anhydrous sodium acetate (chemical abbr. is NaOAc) were dissolved in distilled water, after stirred at 40–60° C. for 5–15 minutes, the resulting reaction mixture was treated with a solution of 3,3-diformyl-2,2'-dihydroxy-1,1'-phenyl in a mixed solvent of ethanol and THF (1:1 volume ratio). Heated to 70–90° C. and stirred for 1–3 hours. To the resulting Schiff base solution was added a 25% aqueous vanadyl sulfate solution. The reaction mixture was stirred for another 2 h at room temperature to give the chiral catalyst. The ratio of chiral amino acid: NaOAc: water: 3,3-diformyl-2,2'-dihydroxy-1,1'-phenyl: $VOSO_4$ was 1.2:2.4:100~150:0.5:1.1 (the molar ratio), mixed solvent: 3,3-diformyl-2,2'-dihydroxy-1,1'-phenyl was 20–25:1 (calculated by weight). In accordance with the present invention, starting from 2-naphthol, binaphthol and its derivatives with high optical purity were synthesized through oxidative coupling catalyzed by 1–10 mol % (calculated by raw material) of chiral catalyst using oxygen as oxidant.

This invention differs from those asymmetric reactions whose enantioselectivity was controlled by the single chiral center, the reaction was influenced by the corporation of chiral amino acid and the axial chirality induced from the condensation of the chiral amino acid and 3,3-diformyl-2, 2'-dihydroxy-1,1'-phenyl, thus improved the enantiomeric excess of the product to 90–97%, which was the best result obtained so far.

Procedure for the preparation of chiral catalyst used in the oxidative coupling in this invention was shown as follows:

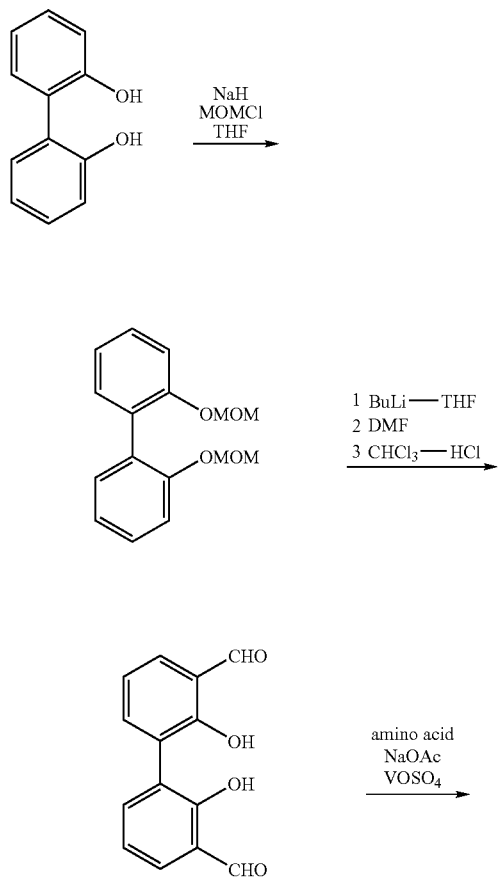

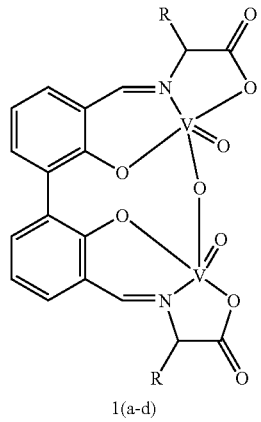

1(a-d)

Through oxidative coupling of naphthol and its derivatives catalyzed by the chiral catalyst, high optical purity of the product was obtained, the procedure was shown as follows:

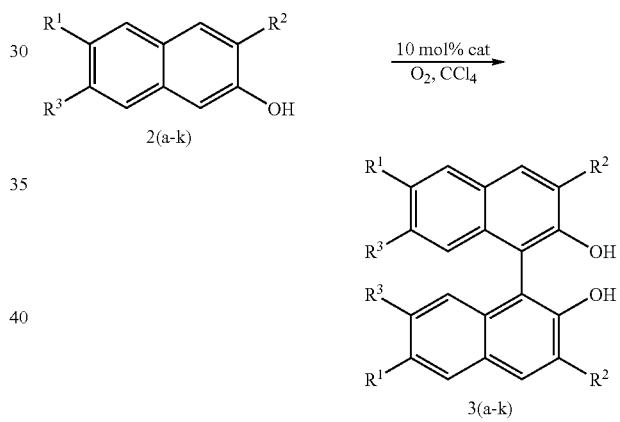

Wherein the raw material was 2a, 2b, 2c, 2d, 2e, 2f, 2g, 2h, 2i, 2j and 2k defined as follows: 2a, $R^1=R^2=R^3=H$; 2b, $R^1=H$, $R^2=H$, $R^3=OMe$; 2c, $R^1=Br$, $R^2=H$, $R^3=H$; 2d, $R^1=H$, $R^2=OMe, R^3=H$; 2e, $R^1=H$, $R^2=H$, $R^3=OEt$; 2f, $R^1=H$, $R^2=OBn$, $R^3=H$; 2g, $R^1=H$, $R^2=H$, $R^3=OBn$; 2h, $R^1=H$, $R^2=H$, $R^3=O^nBu$; 2i, $R^1=H$, $R^2=H$, $R^3=OCH_2CH=CH_2$; 2j, $R^1=H$, $R^2=H$, $R^3=OC_8H_{17}$; 2k, $R^1=H$, $R^2=H$, $R^3=OC_{12}H_{25}$; The corresponding product 3a, 3b, 3c, 3d, 3e, 3f, 3g, 3h, 3i, 3j and 3k were also defined similarly as follows: 3a, $R^1=R^2=R^3=H$; 3b, $R^1=H$, $R^2=H$, $R^3=OMe$; 3c, $R^1=Br$, $R^2=H, R^3=H$; 3d, $R^1=H$, $R^2=OMe$, $R^3=H$; 3e, $R^1=H$, $R^2=H$, $R^3=OEt$; 3f, $R^1=H$, $R^2=OBn$, $R^3=H$; 3g, $R^1=H$, $R^2=H$, $R^3=OBn$; 3h, $R^1=H$, $R^2=H$, $R^3=O^nBu$; 3i, $R^1=H$, $R^2=H$, $R^3=OCH_2CH=CH_2$; 3j, $R^1=H$, $R^2=H$, $R^3=OC_8H_{17}$; 3k, $R^1=H$, $R^2=H$, $R^3=OC_{12}H_{25}$; The catalysts used was 1a, 1b, 1c and 1d defined as follows: 1a: R=Bn, 1b: R=$^i$Pr, 1c: R=$^i$Bu, 1d: R=$^t$Bu. Configuration of the material amino acid was S.

The reaction was performed under 0° C., optical purity was measured by chiral Kromasil CHI-TBB column or Chiralpak AD column.

The results were shown in the following Table 1:

TABLE 1

The Asymmetric oxidative coupling of 2-naphthol and its derivatives catalyzed by 1c under 0° C.

| Entry | Product | Time(d) | Yield (%) | e.e. (%) |
|---|---|---|---|---|
| 1 | 3a | 7 | 84 | 90 |
| 2 | 3b | 7 | 95 | 95 |
| 3 | 3c | 4 | 98 | 90 |
| 4 | 3d | 6 | trace | ND |
| 5 | 3e | 4 | 99 | 96 |
| 6 | 3f | 6 | trace | ND |
| 7 | 3g | 6 | 80 | 95 |
| 8 | 3h | 4 | 99 | 94 |
| 9 | 3i | 4 | 99 | 95 |
| 10 | 3j | 4 | 99 | 94 |
| 11 | 3k | 4 | 94 | 97 |
| 12 | 3a | 8 | 85 | 90 |

Note:
1. The trace in the table indicates lower than 5% of the yield, ND indicate no isolable product was obtained.
2. e.e. (%) indicate enantiomeric excess.
3. Because product 3d and 3f were not isolated, the corresponding products for entry 1, 2, 3, 5, 7, 8, 9, 10, 11, 12 were prepared from the following example 9 to 18.

DESCRIPTION OF THE PREFFERD EMBODIMENTS

Through the description of the optimal examples, this invention was clarified in detail:

EXAMPLE 1

Preparation of 2,2'-Bis-(methoxymethoxy)bibenzene

To a 250 mL of three-necked bottle was added NaH (content 50%, 3.5 g, 72 mmol), anhydrous THF (60 mL) and anhydrous DMF (20 mL), after the temperature was lowered to 0° C., a solution of biphenol (5.6 g, 30 mmol) in THF (15 mL) was added, stirred at this temperature for 10 minutes. Methoxymethyl chloride (6 mL, 78 mmol) was added dropwise, and the mixture was stirred for 8 h at room temperature, quenched by adding 100 mL of water, extracted with ethyl acetate (100 mL×3), the combined organic phase was washed with brine (60 mL×2), dried over MgSO$_4$, after filtration, the solvent was removed to give a yellow oil. Purification through chromatography give 8 g (97% yield) of the product as a light yellow oil. $^1$HNMR (300 MHz, CDCl$_3$) δ (ppm) 3.39 (s, 6H), 5.12 (s, 4H), 7.13 (m, 2H), 7.30–7.37 (m, 6H). Physical data of the compound was consistent with that reported in literature.

EXAMPLE 2

Preparation of 2,2'-Bis-(methoxymethoxy)-3,3'-Diformylbibenzene 2,2'-Bis-(methoxymethoxy)bibenzene (7.5 g, 27.4 mmol) was dissolved in 300 mL of anhydrous Et$_2$O in a 500 mL of three-necked bottle, while stirring, 80 mmol (50 mL, 1.6M solution in hexane) of nBuLi was added dropwise under Ar atmosphere, the mixture was stirred at room temperature for 2 h. After cooled to 0° C., DMF (20 mL, 260 mmol) in THF (20 mL) was added, and the solution was stirred at room temperature for another 4 h. Saturated NH$_4$Cl (150 mL) was added to quench the reaction. The organic layer was separated and the aqueous phase was extracted with ethyl acetate (100 mL×3). The combined organic phase was washed with water (100 mL) and brine (100 mL) successively and dried over anhydrous MgSO$_4$. Concentration with a rotary evaporator and subsequent chromatography on silica gel eluted with petroleum ether/ethyl acetate (3:1) afforded the product 3.925 g (47% yield) as a yellow oil. $^1$HNMR (300 MHz, CDCl$_3$) δ (ppm) 3.15 (s, 6H), 4.81 (s, 4H), 7.37 (dd, J=0.9, 8.4 Hz, 2H), 7.67 (dd, J=1.8, 7.5 Hz, 2H), 7.93 (dd, J=1.8, 7.8 Hz, 2H), 10.44 (s, 2H). Physical data of the compound was consistent with that reported in literature.

EXAMPLE 3

Preparation of 3,3'-Diformyl-2,2'-biphenol 2,2'-Bis-(methoxymethoxy)-3,3'-Diformylbibenzene (3.0 g, 9 mmol), CHCl$_3$ (60 mL), 6M HCl (60 mL) and ethanol (40 mL) was mixed in a 250 mL round-bottom flask, heated to reflux for 14 h. The organic layer was separated and the aqueous phase was extracted with CH$_2$Cl$_2$ (80 mL×2). The combined organic phase was washed with 5% aqueous NaHCO$_3$ (50 mL) and water (80 mL×2) successively and dried over anhydrous Na$_2$SO$_4$. After filtration and concentrated, the yellow solid was recrystallized from ethyl acetate and petroleum ether to give the product 1.92 g (87% yield) as a yellow needle crystal. $^1$HNMR (300 MHz, CDCl$_3$) δ (ppm) 7.13 (dd, 2H), 7.05–7.36 (m, 5H), 9.96 (s, 2H), 11.45 (s, 2H); Physical data of the compound was consistent with that reported in literature.

EXAMPLE 4

Preparation of Chiral Catalyst

L-phenylalanine (1.2 mmol), anhydrous NaOAc (2.4 mmol) and distilled water (1 mL) were placed in a two-neck round bottom flask (10 mL) charged with Ar. After stirred at 60° C. for about 10 min, the resulting reaction mixture was treated with a solution of 3,3'-Diformyl-2,2'-biphenol (0.5 mmol) in EtOH (5 mL) and THF (5 mL). The reaction mixture was refluxed at 90° C. for 1.5 h, and then was gradually cooled down to room temperature. To the resulting Schiff base solution was added a solution of vanadyl sulfate trihydrate (1.1 mmol) in water (1 mL). The reaction mixture was stirred for another 2 h and then concentrated. 10 mL H$_2$O was added and the mixture was extracted with CH$_2$Cl$_2$ (3×20 mL), the combined organic layer was washed with water (3×20 mL) and then dried over anhydrous Na$_2$SO$_4$ Removal of solvent gave vanadyl complex 1a as a dark solid. HRMS: 683.0434 (M+H), calculated for C$_{32}$H$_{25}$N$_2$O$_9$V$_2$: 683.0439. IR (cm$^{-1}$): $v_{C=N}$ (1685), $v_{C=O}$ (1623), $v_{V=O}$ (986).

EXAMPLE 5

Preparation of Chiral Catalyst

S-Valine (1.2 mmol), anhydrous NaOAc (2.4 mmol) and distilled water (1 mL) were placed in a two-neck round bottom flask (10 mL) charged with Ar. After stirred at 60° C. for about 10 min, the resulting reaction mixture was treated with a solution of 3,3'-Diformyl-2,2'-biphenol (0.5 mmol) in EtOH (5 mL) and THF (5 mL). The reaction mixture was refluxed at 90° C. for 1.5 h, and then was gradually cooled down to room temperature. To the resulting Schiff base solution was added a solution of vanadyl sulfate trihydrate (1.1 mmol) in water (1 mL). The reaction mixture was stirred for another 2 h and then concentrated. 10 mL H₂O was added and the mixture was extracted with CH₂Cl₂ (3×20 mL), the combined organic layer was washed with water (3×20 mL) and then dried over anhydrous Na₂SO₄. Removal of solvent gave vanadyl complex 1b as a dark solid. HRMS: 587.0418 (M+H), Calculated for $C_{24}H_{25}N_2O_9V_2$: 587.0439. IR: $\nu_{C=N}$ (1687), $\nu_{C=O}$ (1620), $\nu_{V=O}$ (989).

EXAMPLE 6

Preparation of Chiral Catalyst

L-isoleucine (1.2 mmol), anhydrous NaOAc (2.4 mmol) and distilled water (1 mL) were placed in a two-neck round bottom flask (10 mL) charged with Ar. After stirred at 60° C. for about 10 min, the resulting reaction mixture was treated with a solution of 3,3'-Diformyl-2,2'-biphenol (0.5 mmol) in EtOH (5 mL) and THF (5 mL). The reaction mixture was refluxed at 90° C. for 1.5 h, and then was gradually cooled down to room temperature. To the resulting Schiff base solution was added a solution of vanadyl sulfate trihydrate (1.1 mmol) in water (1 mL). The reaction mixture was stirred for another 2 h and then concentrated. 10 mL H₂O was added and the mixture was extracted with CH₂Cl₂ (3×20 mL), the combined organic layer was washed with water (3×20 mL) and then dried over anhydrous Na₂SO₄ Removal of solvent gave vanadyl complex 1c as a dark solid. HRMS: 615.0728 (M+H), Calculated for $C_{26}H_{29}N_2O_9V_2$: 615.075. IR: $V_{C=N}$ (1696), $\nu_{C=O}$ (1618), $\nu_{V=O}$ (992).

EXAMPLE 7

Preparation of Chiral Catalyst

L-tert-Leucine (1.2 mmol), anhydrous NaOAc (2.4 mmol) and distilled water (1 mL) were placed in a two-neck round bottom flask (10 mL) charged with Ar. After stirred at 60° C. for about 10 min, the resulting reaction mixture was treated with a solution of 3,3'-Diformyl-2,2'-biphenol (0.5 mmol) in EtOH (5 mL) and THF (5 mL). The reaction mixture was refluxed at 90° C. for 1.5 h, and then was gradually cooled down to room temperature. To the resulting Schiff base solution was added a solution of vanadyl sulfate trihydrate (1.1 mmol) in water (1 mL). The reaction mixture was stirred for another 2 h and then concentrated. 10 mL H₂O was added and the mixture was extracted with CH₂Cl₂ (3×20 mL), the combined organic layer was washed with water (3×20 mL) and then dried over anhydrous Na₂SO₄. Removal of solvent gave vanadyl complex 1d as a dark solid. HRMS: 615.0635 (M+H), calculated for $C_{26}H_{29}N_2O_9V_2$: 615.0752. IR: $V_{C=N}$ (1683), $\nu_{C=O}$ (1615), $\nu_{V=O}$ (994).

EXAMPLE 8

Preparation of Chiral Catalyst

R-phenylalanine (1.2 mmol), anhydrous NaOAc (2.4 mmol) and distilled water (1 mL) were placed in a two-neck round bottom flask (10 mL) charged with Ar. After stirred at 60° C. for about 10 min, the resulting reaction mixture was treated with a solution of 3,3'-Diformyl-2,2'-biphenol (0.5 mmol) in EtOH (5 mL) and THF (5 mL). The reaction mixture was refluxed at 90° C. for 1.5 h, and then was gradually cooled down to room temperature. To the resulting Schiff base solution was added a solution of vanadyl sulfate trihydrate (1.1 mmol) in water (1 mL). The reaction mixture was stirred for another 2 h and then concentrated. 10 mL H₂O was added and the mixture was extracted with CH₂Cl₂ (3×20 mL), the combined organic layer was washed with water (3×20 mL) and then dried over anhydrous Na₂SO₄ Removal of solvent gave the chiral catalyst.

EXAMPLE 9

Oxidative Coupling of 2-naphthol and its Derivatives Catalyzed by 1c

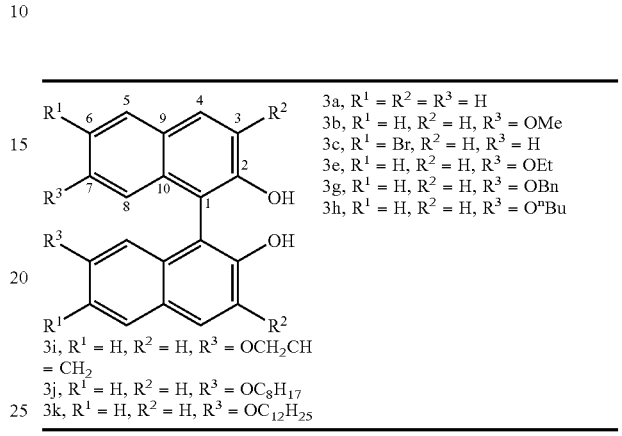

3a, $R^1 = R^2 = R^3 = H$
3b, $R^1 = H, R^2 = H, R^3 = OMe$
3c, $R^1 = Br, R^2 = H, R^3 = H$
3e, $R^1 = H, R^2 = H, R^3 = OEt$
3g, $R^1 = H, R^2 = H, R^3 = OBn$
3h, $R^1 = H, R^2 = H, R^3 = O^nBu$
3i, $R^1 = H, R^2 = H, R^3 = OCH_2CH=CH_2$
3j, $R^1 = H, R^2 = H, R^3 = OC_8H_{17}$
3k, $R^1 = H, R^2 = H, R^3 = OC_{12}H_{25}$

A two-neck round bottom flask (5 mL) was charged with a solution of catalyst 1c (12.2 mg, 0.02 mmol) in anhydrous CCl₄ (1 mL). The solution was stirred for 10 min under an oxygen atmosphere and then treated with a solution of 2-naphthol (29 mg, 0.2 mmol) in anhydrous CCl₄ (1 mL). The reaction mixture was stirred at 0° C. until the reaction was complete (monitored by TLC). The crude mixture was concentrated under reduced pressure, and purified by column chromatography (Ethyl acetate/Petroleum ether=⅓) to give (R)-BINOL 3a, Yield 84%. ¹HNMR (300 MHz, CDCl₃) δ (ppm) 7.98 (d, J=9.0 Hz, 2H, 2×HC (4)), 7.90 (d, J=7.8 Hz, 2H, 2×HC (5)), 7.38 (d, J=9.0 Hz, 2H, 2×HC (8)), 7.41–7.27 (m, 4H, 2×HC (6), 2×HC (7)), 7.16 (d, J=8.4 Hz, 2 H, 2×HC (3)), 5.09 (s, 2H, 2×OH). e.e. 90% and the configuration was R (Kromasil CHI-TBB column, Hexane/propan-2-ol=90:10; flow rate 1 mL/min; S-isomer, $t_R$ 7.78 min and R-isomer, $t_R$ 8.79 min).

EXAMPLE 10

Oxidative Coupling of 2-naphthol and its Derivatives Catalyzed by 1c

A reaction flask described in example 9 was charged with a solution of catalyst 1c (12.2 mg, 0.02 mmol) in anhydrous CCl₄ (1 mL). The solution was stirred for 10 min under an oxygen atmosphere and then treated with a solution of 7-methoxy-2-naphthol (35 mg, 0.2 mmol) in anhydrous CCl₄ (1 mL) under 0° C. The reaction mixture was stirred at 0° C. until the reaction was complete (monitored by TLC). The crude mixture was concentrated under reduced pressure, and purified by column chromatography (Ethyl acetate/Petroleum ether=⅓) to give (R)-BINOL 3b, Yield 95%. $[\alpha]_D^{25}=-104.7$ (c=0.35 in EtOAc), ¹HNMR (300 MHz, CDCl₃) δ (ppm) 7.88 (d, J=9.0 Hz, 2H, 2×HC (5)), 7.79 (d, J=9.0 Hz, 2H, 2×HC (4)), 7.22 (d, J=8.7 Hz, 2H, 2×HC (3)), 7.03 (dd, J=9.0 Hz, 2.4 Hz, 2H, 2×HC (6)), 6.49 (d, J=2.4 Hz, 2H, 2×HC (8)), 5.08 (s, 2H, 2×OH), 3.59 (s, 6H, 2×OCH₃). e.e. 95%, and the configuration was R (Kromasil CHI-TBB column, Hexane/propan-2-ol=80: 20; flow rate 1 mL/min; S-isomer, $t_R$ 4.95 min and R-isomer, $t_R$ 5.32 min).

EXAMPLE 11

Oxidative Coupling of 2-naphthol and its Derivatives Catalyzed by 1c

A reaction flask described in example 9 was charged with a solution of catalyst 1c (12.2 mg, 0.02 mmol) in anhydrous $CCl_4$ (1 mL). The solution was stirred for 10 min under an oxygen atmosphere and then treated with a solution of 6-bromo-2-naphthol (44 mg, 0.2 mmol) in anhydrous $CCl_4$ (1 mL) under 0° C. The reaction mixture was stirred at 0° C. until the reaction was complete (monitored by TLC). The crude mixture was concentrated under reduced pressure, and purified by column chromatography (Ethyl acetate/Petroleum ether-⅓) to give (R)-BINOL 3c, Yield 99%. $[\alpha]_D^{25}=-33.7$ (c=0.4 in EtOAc), $^1$H NMR (300 MHz, $CDCl_3$) δ (ppm) 8.06 (d, J=1.8 Hz, 2H, 2×HC (4)), 7.89 (d, J=9.0 Hz, 2H, 2×HC (5)), 7.37 (d, J=6.9 Hz, 2H, 2×HC (8)), 7.36 (dd, J=9.0 Hz, 1.8 Hz, 2H, 2×HC (7)), 6.96 (d, J=9.0 Hz, 2H, 2×HC (3)), 5.08 (s, 2H, 2×OH). e.e. 90%, and the configuration was R (Kromasil CHI-TBB column, Hexane/propan-2-ol=80: 20; flow rate 1 mL/min; S-isomer, $t_R$ 6.68 min and R-isomer, $t_R$ 7.51 min).

EXAMPLE 12

Oxidative Coupling of 2-naphthol and its Derivatives Catalyzed by 1c

A reaction flask described in example 9 was charged with a solution of catalyst 1c (12.2 mg, 0.02 mmol) in anhydrous $CCl_4$ (1 mL). The solution was stirred for 10 min under an oxygen atmosphere and then treated with a solution of 7-ethoxy-2-naphthol (38 mg, 0.2 mmol) in anhydrous $CCl_4$ (1 mL) under 0° C. The reaction mixture was stirred at 0° C. until the reaction was complete (monitored by TLC). The crude mixture was concentrated under reduced pressure, and purified by column chromatography (Ethyl acetate/Petroleum ether=⅓) to give (R)-BINOL 3e, Yield 99%. $[\alpha]_D^{25}=-154.0$ (c=0.4 in EtOAc), $^1$HNMR (300 MHz, $CDCl_3$) δ (ppm) 7.87 (d, J=9.0 Hz, 2H, 2×HC (5)), 7.78 (d, J=9.0 Hz, 2H, 2×HC (4)), 7.21 (d, J=9.0 Hz, 2H, 2×HC (3)), 7.03 (dd, J=9.0 Hz, 2.4 Hz, 2H, 2×HC (6)), 6.49 (d, J=2.1 Hz, 2H, 2×HC (8)), 5.06 (s, 2H, 2×OH), 3.78 (m, 4H, 4×OCH$_2$), 1.28 (t, 6H, 6×CH$_3$). e.e. 96%.

EXAMPLE 13

Oxidative Coupling of 2-naphthol and its Derivatives Catalyzed by 1c

A reaction flask described in example 9 was charged with a solution of catalyst 1c (12.2 mg, 0.02 mmol) in anhydrous $CCl_4$ (1 mL). The solution was stirred for 10 min under an oxygen atmosphere and then treated with a solution of 7-benzyloxy-2-naphthol (50 mg, 0.2 mmol) in anhydrous $CCl_4$ (1 mL) under 0° C. The reaction mixture was stirred at 0° C. until the reaction was complete (monitored by TLC). The crude mixture was concentrated under reduced pressure, and purified by column chromatography (Ethyl acetate/Petroleum ether=⅓) to give (R)-BINOL 3g, Yield 80%. $[\alpha]_D^{25}=-157.4$ (c=0.3 in EtOAc), $^1$HNMR (300 MHz, $CDCl_3$) δ (ppm) 7.89 (d, J=9.0 Hz, 2H, 2×HC (5)), 7.80 (d, J=8.7 Hz, 2H, 2×HC (4)), 7.24 (d, J=9.0 Hz, 2H, 2×HC (3)), 7.10–7.22 (m, 12H, 2×HC (6), 10×PhH), 6.50 (d, J=2.1 Hz, 2H, 2×HC (8)), 5.01 (s, 2H, 2×OH), 4.73.4.84 (m, 4H, 4×OCH$_2$). e.e. 95%.

EXAMPLE 14

Oxidative Coupling of 2-naphthol and its Derivatives Catalyzed by 1c

A reaction flask described in example 9 was charged with a solution of catalyst 1c (12.2 mg, 0.02 mmol) in anhydrous $CCl_4$ (1 mL). The solution was stirred for 10 min under an oxygen atmosphere and then treated with a solution of 7-n-butyloxy-2-naphthol (43 mg, 0.2 mmol) in anhydrous $CCl_4$ (1 mL) under 0° C. The reaction mixture was stirred at 0° C. until the reaction was complete (monitored by TLC). The crude mixture was concentrated under reduced pressure, and purified by column chromatography (Ethyl acetate/Petroleum ether=⅓) to give (R)-BINOL 3h, Yield 99%. $[\alpha]_D^{25}=-168.4$ (c=0.4 in EtOAc), $^1$HNMR (300 MHz, $CDCl_3$) δ (ppm) 7.87 (d, J=9.0 Hz, 2H, 2×HC (5)), 7.78 (d, J=9.0 Hz, 2H, 2×HC (4)), 7.21 (d, J=9.0 Hz, 2H, 2×HC (3)), 7.03 (dd, J=9.0 Hz, 3.0 Hz, 2H, 2×HC (6)), 6.49 (s, 2H, 2×HC (8)), 5.08 (s, 2H, 2×OH), 3.68 (m, 4H, 4×OCH$_2$), 1.58–1.67 (m, 4H, 4×OCH$_2$CH$_2$), 1.28–1.40 (m 4H, 4×CH$_3$CH$_2$), 0.85–0.89 (t, 6H, 6×CH$_3$). e.e. 94%.

EXAMPLE 15

Oxidative Coupling of 2-naphthol and its Derivatives Catalyzed by 1c

A reaction flask described in example 9 was charged with a solution of catalyst 1 c (12.2 mg, 0.02 mmol) in anhydrous $CCl_4$ (1 mL). The solution was stirred for 10 min under an oxygen atmosphere and then treated with a solution of 7-allyloxy-2-naphthol (40 mg, 0.2 mmol) in anhydrous $CCl_4$ (1 mL) under 0° C. The reaction mixture was stirred at 0° C. until the reaction was complete (monitored by TLC). The crude mixture was concentrated under reduced pressure, and purified by column chromatography (Ethyl acetate/Petroleum ether=⅓) to give (R)-BINOL 3i, Yield 99%. $[[\alpha]_D^{25}=-186.5$ (c=0.4 in EtOAc), $^1$HNMR (300 MHz, $CDCl_3$) δ (ppm) 7.87 (d, J=9.0 Hz, 2H, 2×HC (5)), 7.78 (d, J=9.0 Hz, 2H, 2×HC (4)), 7.21 (d, J=9.0 Hz, 2H, 2×HC (3)), 7.03 (dd, J=9.0 Hz, 3.0 Hz, 2H, 2×HC (6)), 6.49 (s, 2H, 2×HC (8)), 5.08 (s, 2H, 2×OH), 3.66–3.78 (m, 4H, 4×OCH$_2$), 1.58–1.67 (m, 4H, 4×OCH$_2$CH$_2$), 1.20–1.40 (m, 4H, 4×CH$_2$CH$_3$), 0.87–0.89 (t, 6H, 6×CH$_3$). e.e. 95%.

EXAMPLE 16

Oxidative Coupling of 2-naphthol and its Derivatives Catalyzed by 1c

A reaction flask described in example 9 was charged with a solution of catalyst 1c (12.2 mg, 0.02 mmol) in anhydrous $CCl_4$ (1 mL). The solution was stirred for 10 min under an oxygen atmosphere and then treated with a solution of 7-octyloxy-2-naphthol (54 mg, 0.2 mmol) in anhydrous $CCl_4$ (1 mL) under 0° C. The reaction mixture was stirred at 0° C. until the reaction was complete (monitored by TLC). The crude mixture was concentrated under reduced pressure, and purified by column chromatography (Ethyl acetate/Petroleum ether=⅓) to give (R)-BINOL 3j, Yield 99%. $[\alpha]_D^{25}=-153.8$ (c=0.5 in EtOAc), $^1$HNMR (300 MHz, $CDCl_3$) δ (ppm) 7.87 (d, J=9.0 Hz, 2H, 2×HC (5)), 7.78 (d, J=9.0 Hz, 2H, 2×HC (4)), 7.21 (d, J=9.0 Hz, 2H, 2×HC (3)), 7.03 (dd, J=9.0 Hz, 2.4 Hz, 2H, 2×HC (6)), 6.49 (d, J=2.1 Hz, 2H, 2×HC (8)), 5.07 (s, 2H, 2×OH), 3.67–3.77 (m, 4H, 4×OCH$_2$), 1.59–1.66 (m, 4H, 4×OCH$_2$CH$_2$), 1.25–1.29 (m, 20H, 20×CH$_2$), 0.86–0.90 (t, 6H, 6×CH$_3$). e.e. 94%.

EXAMPLE 17

Oxidative Coupling of 2-naphthol and its Derivatives Catalyzed by 1c

A reaction flask described in example 9 was charged with a solution of catalyst 1c (12.2 mg, 0.02 mmol) in anhydrous $CCl_4$ (1 mL). The solution was stirred for 10 min under an oxygen atmosphere and then treated with a solution of 7-dodecyloxy-2-naphthol (66 mg, 0.2 mmol) in anhydrous $CCl_4$ (1 mL) under 0° C. The reaction mixture was stirred at 0° C. until the reaction was complete (monitored by TLC). The crude mixture was concentrated under reduced pressure, and purified by column chromatography (Ethyl acetate/Petroleum ether=⅓) to give (R)-BINOL 3k, Yield 94%. $[\alpha]_D^{25}=-86.3$ (c=0.2 in EtOAc), $^1$HNMR (300 MHz, $CDCl_3$) δ (ppm) 7.86 (d, J=9.0 Hz, 2H, 2×HC (5)), 7.78 (d, J=9.0 Hz, 2H, 2×HC (4)), 7.21 (d, J=9.0 Hz, 2H, 2×HC (3)), 7.03 (dd, J=9.0 Hz, 2.1 Hz, 2H, 2×HC (6)), 6.49 (d, J=2.1 Hz, 2H, 2×HC (8)), 5.08 (s, 2H, 2×OH), 3.65–3.79 (m, 4H, 4×$OCH_2$), 1.59–1.67 (m, 4H, 4×$OCH_2CH_2$), 1.25–1.27 (m, 36H, 36 ×$CH_2$), 0.88–0.92 (t, 6H, 6×$CH_3$). e.e. 97%.

EXAMPLE 18

A two-neck round bottom flask (50 mL) was charged with a solution of catalyst 1c (122 mg, 0.2 mmol) in anhydrous $CCl_4$ (10 mL). The solution was stirred for 10 min under an oxygen atmosphere and then treated with a solution of 2-naphthol (290 mg, 2 mmol) in anhydrous $CCl_4$ (10 mL). The reaction mixture was stirred at 0° C. until the reaction was complete (monitored by TLC). The crude mixture was concentrated under reduced pressure, and purified by column chromatography (Ethyl acetate/Petroleum ether=⅓) to give (R)-BINOL 3a, Yield 85%. $^1$HNMR (300 MHz, $CDCl_3$) δ (ppm) 7.98 (d, J=9.0 Hz, 2H, 2×HC (4)), 7.90 (d, J=7.8 Hz, 2H, 2×HC (5)), 7.38 (d, J=9.0 Hz, 2H, 2×HC (8)), 7.41–7.27 (m, 4H, 2×HC (6), 2×HC (7)), 7.16 (d,J=8.4 Hz, 2H, 2×HC (3)), 5.09 (s, 2H, 2×OH). e.e. 90% and the configuration was R (Kromasil CHI-TBB column, Hexane/propan-2-ol=90:10; flow rate 1 mL/min; S-isomer, $t_R$ 7.78 min and R-isomer, $t_R$ 8.79 min).

It should be noted that from the technique common sense, the invention can be implemented from other examples with similar characteristic to those mentioned above. Therefore, above-mentioned public implement project, in regard to every aspect, all just illustrate with example, is not only. All within the scope of the invention or within the scope of changes equal to the invention was all included by the invention.

What is claimed is:

1. A chiral catalyst used for oxidative coupling of naphthols, comprising vanadium complex of Schiff's base a chiral amino acid and a formyl biphenol or its derivatives, having the general formula:

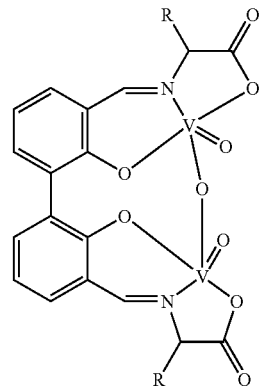

where R represents a benzyl, an isopropyl, an isobutyl or a tertiary butyl and the configuration of the amino acid is R or S.

2. The chiral catalyst according to claim 1, wherein said R is a benzyl when the configuration of the amino acid is S.

3. The chiral catalyst according to claim 1, wherein said R is an isopropyl when the configuration of the amino acid is S.

4. The chiral catalyst according to claim 1, wherein said R is an isobutyl when the configuration of the amino acid is S.

5. The chiral catalyst according to claim 1, wherein said R is a tertiary butyl when the configuration of the amino acid is S.

6. The chiral catalyst according to claim 1, wherein said R is a benzyl when the configuration of the amino acid is R.

7. The chiral catalyst according to claim 1, wherein said R is an isopropyl when the configuration of the amino acid is R.

8. The chiral catalyst according to claim 1, wherein said R IS an isobutyl when the configuration of the amino acid is R.

9. The chiral catalyst according to claim 1, wherein said R is a tertiary butyl when the configuration of the amino acid is R.

10. A process for preparing a chiral catalyst used for oxidative coupling of naphthols, comprising the following steps:
   a. making a solution of a chiral amino acid and sodium acetate dissolved in water;
   b. adding a solution of 3,3'-diformyl-2,2'-dihydroxy-1,1'phenyl in a mixed reagent of EtOH and THF to the solution obtained by step a, and stirring the reaction mixture for 1~3 hours at 70~90° C.; and
   c. adding an aqueous solution of 25% $VOSO_4$ to the resulting mixture, cooling it to ambient temperature, then stirring it for 1~3 hours to produce the catalyst.

11. The process for preparing a chiral catalyst according to claim 10, further comprising
stirring the solution of step a for 5~15 minutes at 40~60° C.

12. The process for preparing a chiral catalyst according to claim 10, further comprising combining the mixed reagent and 3,3'-diformyl-2,2'-dihydroxy-1,1'phenyl in a ratio of 20~5:1, and in the mixed reagent, combining the EtOH to THF in a volume ratio of about 1:1.

13. The process for preparing a chiral catalyst according to claim 10, wherein the molar ratio of the chiral amino acid, sodium acetate, water, 3'3-bi-formly-biphenol to $VOSO_4$ of steps a, b and c is 1.2:2.4:100~150:0.5:1.1.

14. A method of using a chiral catalyst used for oxidative coupling of naphthol for the preparation of binaphthol or its derivatives, comprising catalyzing naphthol or its derivatives with oxygen as an oxidizing agent with 1~10 mol % of the chiral catalyst of claim 1 to produce highly optically pure binaphthol or its derivatives.

* * * * *